United States Patent [19]

Williams et al.

[11] Patent Number: 4,959,402

[45] Date of Patent: * Sep. 25, 1990

[54] HIGH CLARITY RADIATION STABLE POLYMERIC COMPOSTION AND ARTICLES THEREFROM

[75] Inventors: Joel L. Williams, Cary; George R. Titus, Raleigh, both of N.C.

[73] Assignee: Becton, Dickinson and Company, Franklin Lakes, N.J.

[*] Notice: The portion of the term of this patent subsequent to Jul. 4, 2006 has been disclaimed.

[21] Appl. No.: 362,999

[22] Filed: Jun. 8, 1989

[51] Int. Cl.$^5$ .......................... C08K 5/34; C08K 5/15
[52] U.S. Cl. .................................. 524/99; 524/108; 524/583; 524/585; 524/567; 252/406
[58] Field of Search ................... 524/99, 108; 252/406

[56] References Cited

U.S. PATENT DOCUMENTS

| | | |
|---|---|---|
| 4,016,118 | 4/1977 | Hamada et al. |
| 4,110,185 | 8/1978 | Williams et al. |
| 4,274,932 | 6/1981 | Williams et al. |
| 4,371,645 | 2/1983 | Mahaffey, Jr. .................. 524/108 |
| 4,563,259 | 1/1986 | Rayner. |
| 4,710,524 | 12/1987 | Donohue .............................. 524/99 |
| 4,785,034 | 11/1988 | Gaku et al. ........................... 524/99 |
| 4,808,650 | 2/1989 | Titus et al. .......................... 524/108 |
| 4,845,137 | 7/1989 | Williams et al. .................... 524/108 |

FOREIGN PATENT DOCUMENTS 60-099147  6/1985  Japan ..................................... 524/99

*Primary Examiner*—Joseph L. Schofer
*Assistant Examiner*—Mark Sweet
*Attorney, Agent, or Firm*—Richard Brown

[57] ABSTRACT

A high clarity polymeric composition which is stable toward sterilizing radiation includes a semicrystalline polyolefin of narrow molecular weight distribution having incorporated therein a liquid mobilizing additive, a radiation stabilizing amount of a hindered amine and a clarifying agent. The invention includes a sterilized article fabricated from the composition and a method to radiation sterilize the article.

7 Claims, 4 Drawing Sheets

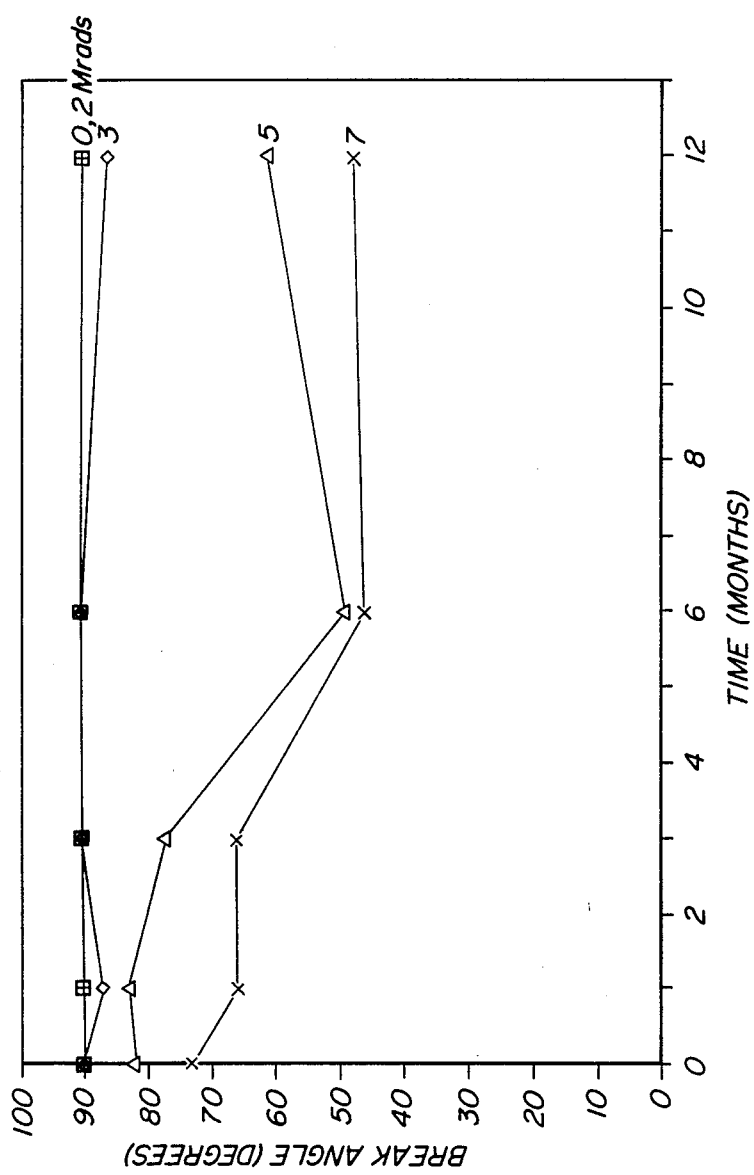

HIGH CLARITY RADIATION STABLE POLYMERIC COMPOSTION AND ARTICLES THEREFROM

BACKGROUND OF THE INVENTION

1. Field of the Invention.

The present invention relates to polymeric articles and more particularly relates to polymeric materials of high clarity and resistance to sterilizing radiation and method of preparing same.

2. Background of the Invention.

Semicrystalline polymeric materials, including the polyolefins of which polypropylene is most significant with respect to the present invention, are often employed in producing articles subsequently subjected to irradiation sterilization techniques. For example, in the health and medical field, these sterilizable articles include syringes, tubing and tube assemblies, microbiological plastics, flasks, package film and the like. It is well known that these semicrystalline polymeric materials, if not properly stabilized, will discolor and become embrittled as a result of sterilization by exposure to high energy radiation at levels above 0.1 megarads.

Further, after irradiation has been completed, post irradiative oxidation continues due to free radicals generated by the irradiation which participate in branching chain reactions. Therefore, while degradation of the mechanical properties of these polymeric materials may not be obvious immediately after irradiation, they become more pronounced as time goes on. Thus, much effort has been expended toward agents or additives which would stabilize polymeric materials toward post irradiation degradation.

Some recent attempts have been made to improve the stability of semicrystalline polymeric materials so as to reduce embrittlement. U.S. Pat. No. 4,110,185 discloses flexible sterilized articles comprising a semicrystalline polymer having a noncrystalline mobilizing additive incorporated therein. The additive increases the free volume of the polymer which is believed to account for the improved stability during and subsequent to irradiation.

In U.S. Pat. No. 4,274,932, a further improvement in radiation stability is achieved by including the above mobilizing additive in a semicrystalline polymer having a narrow molecular weight distribution.

U.S. Pat. No. 4,563,259 to Rayner discloses a substantially crystalline polyolefin of defined molecular weight distribution containing a sterically hindered amine stabilizing agent.

In some applications, as, for example in the packaging industry, polymeric materials are used in forms such as plates, sheets, films and the like in which clarity or transparency is a very desirable property. Clarity may also be important for certain plastic articles, such as syringes, made by injection molding.

In general, clarity is not an inherent property of polyolefin plastics, most of which are more or less opaque due principally to their partially amorphous nature. Most polyolefins do, however, have some crystallinity, and they are generally referred to as semicrystalline. High clarity is thought to be related to a low degree of crystallinity. Size and number of crystals, however, is also important. Large crystals reduce clarity, an effect generally thought to be due to diffraction and scattering of light, and most polyolefins of good clarity are predominantly microcrystalline. It is generally thought that the crystal size should be at or smaller than the wavelength of visible light to prevent light scattering, which causes opacity.

Various additives which improve the clarity of polymeric articles have been described. U.S. Pat. No. 4,016,118 proposes dibenzylidene sorbitol as an additive for improving the transparency of polyolefin articles. Mahaffey et al., in U.S. Pat. No. 4,371,645, discloses dibenzylidene sorbitol additives substituted with hydroxy, methoxy, amino, nitro and halogen groups having greater clarity enhancing effects than the parent unsubstituted compound.

In U.S. Patent application Ser. No. 116,830, filed on Nov. 3, 1987, now U.S. Pat. No. 4,845,137, and of common assignee with the present invention, alkylthio dibenzylidene sorbitol derivatives having antioxidant and clarifying properties are disclosed. This application is herein incorporated by reference.

There is a need, unaddressed hitherto in the art, for a high clarity polyolefin composition capable of radiation sterilization without discoloration or degradation of mechanical properties. It is toward fulfillment of this need that the present invention is directed.

SUMMARY OF THE INVENTION

One aspect of the present invention is a polymeric composition of high clarity which may be radiation sterilized without degradation of its mechanical properties due to the radiation. The composition includes a polyolefin having a narrow molecular weight distribution, a liquid mobilizing additive miscible with the polyolefin which increases the free volume of the polyolefin, a radiation stabilizing amount of a hindered amine and a dibenzylidene sorbitol clarifying agent.

The polyolefin may be a homopolymer or a copolymer of preferably polypropylene having a ratio of the weight average molecular weight to the number average molecular weight of no greater than 9, preferably about 2 to 4. The preferred mobilizer has a density of about 0.6 to 1.9 and most preferably is hydrocarbon oil or a phthalic ester. The preferred stabilizer is a hindered piperidine ester of a dicarboxylic acid and the preferred clarifier is a thioether of a dibenzylidene sorbitol.

A second aspect of the invention is an article, preferably a sterilized medical article fabricated from the composition of the invention. Preferred sterilized articles are syringes, catheters, tube assemblies, tissue culture flasks and package films.

The invention includes a method for preparing a sterilized composition or article by subjecting the composition or article to a sterilizing dose of high energy radiation, preferably from a cobalt-60 source.

In accordance with the principles of the present invention, polymeric materials, such as the polyolefins, and particularly, polypropylene, are sterilizable and rendered stable to high energy irradiation. The combination of a hindered piperidine and a liquid mobilizer, selected from the group of materials as explained below, provides a level of stabilization that the individual materials, acting alone, would not normally impart to polymeric material subjected to high does of radiation. Post irradiative oxidative degradation is substantially reduced in polymeric materials containing these radiation stabilizing additives so that the mechanical properties of the polymer are not compromised. At the same time, the preferred combinations of polymer and radiation stabilizing additives not only show good resistance to post irradiative oxidation but also resist discoloration while retaining flexibility. In addition, high clarity, as characterized by greatly reduced haze, is introduced to the polymer with an additive which is compatible with the sterilizing radiation. These features are highly advantageous, particularly when the improved polymeric materials are made into articles such as syringes, film packages and other medical products which are normally sterilized before use.

BRIEF DESCRIPTION OF THE DRAWINGS

FIG. 4 shows resistance to embrittlement of the polypropylene formulation of FIG. 1 additionally containing a clarifying nucleator.

DETAILED DESCRIPTION

Figure 1:
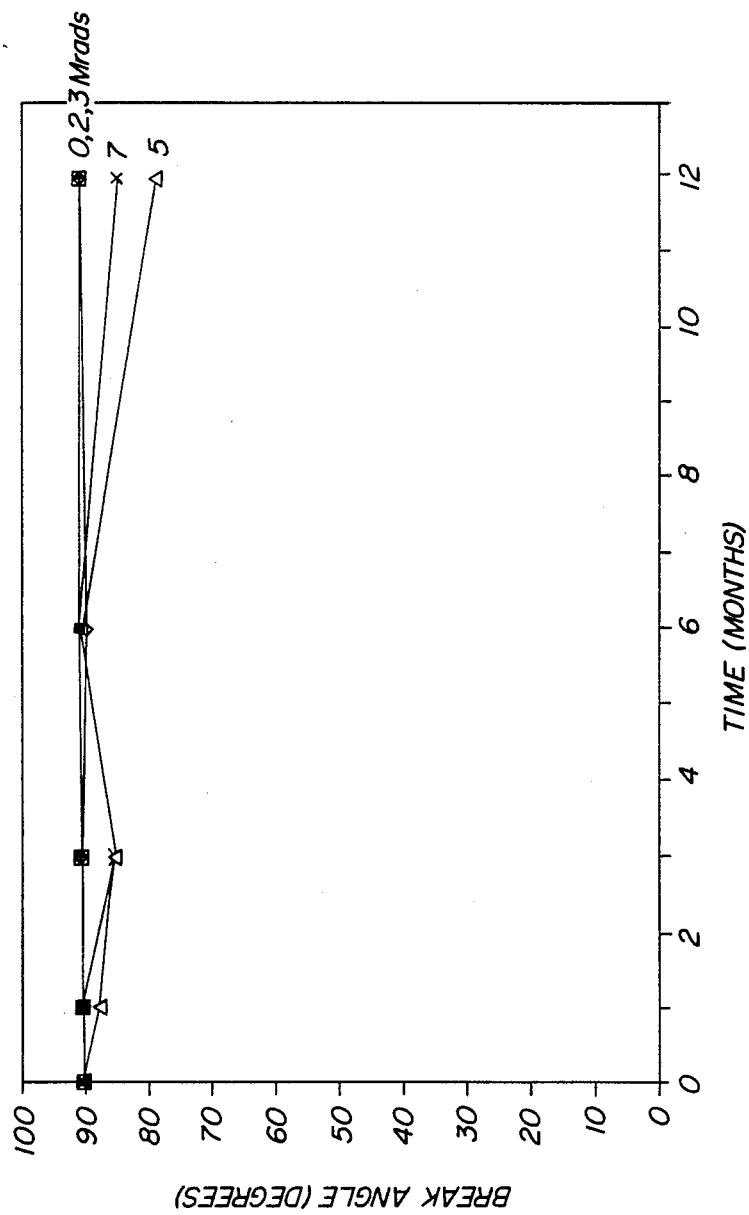
FIG. 1 shows resistance to embrittlement of a narrow molecular weight range polypropylene containing a mobilizing additive.

While this invention is satisfied by embodiments in many different forms, there will herein be described in detail preferred embodiments of the invention, with the understanding that the present disclosure is to be considered as exemplary of the principles of the invention and is not intended to limit the invention to the embodiments illustrated and described. The scope of the invention will be measured by the appended claims and their equivalents.

The polyolefins of the present invention may be described as basically linear, but may optionally contain side chains such as are found, for instance, in conventional, low density polyethylene. It may be a homopolymer or a copolymer of an aliphatic monoolefin, preferably having about 2 to 6 carbon atoms. Exemplary of such polyolefins are polyethylene, polymethylpentene, polytetrafluoroethylene and the like. The preferred polyolefin is polypropylene.

The polyolefin may contain a small amount, generally from about 0.1 to 10 percent of an additional polymer incorporated into the composition by copolymerization with the appropriate monomer. Such copolymers may be added to the composition to enhance other characteristics of the final composition, and may be, for example, polyacrylate, polyvinyl, polystyrene and the like.

It is preferred that the polyolefin of the composition be of narrow molecular weight distribution. The molecular weight distribution of a polymer is defined by the ratio of the weight average molecular weight (Mw) and the number average molecular weight (Mn) wherein the minimum possible ratio of 1.0 defines the polymer having all the chains the same size. Suitable polyolefins for the composition of the invention may have a number average molecular weight of about 10,000 to 400,000, preferably 30,000 to 50,000 and a ratio of from 1 to 9 preferably about 2 to 6, as determined by conventional gel permeation chromatography. Most preferably the ratio is about 2 to 4.

The composition of the invention includes at least two additives which contribute to radiation stability. The first stabilizing additive, hereinafter additive A, is a mobilizing additive of the type described in U.S. Pat. No. 4,274,932. The mobilizer may be a low molecular weight noncrystalline substance which is miscible with the polymeric material and is also compatible therewith, i.e., the mobilizer does not adversely affect the properties of the polymer. The mobilizer may be a substance which increases the free volume of the polymer and, therefore, also lowers the density of the polymer. The mobilizer functions to mobilize the amorphous portion of the polymer, and as a result, increases the radical termination reactions which prevent or minimize degradation during and subsequent to the irradiation.

A wide variety of liquids which increase the total free volume of the polymer may serve as the mobilizer. The term liquid as used herein includes highly viscous substances, commonly referred to as greases. In general, such mobilizers have a density of from 0.6 to 1.9 g/cm$^3$ and preferably of from 0.6 to 1.1 g/cm$^3$. The mobilizer preferably has a low molecular weight, with the average molecular weight generally being in order of from 100 to 10,000 grams/mole, most preferably from 100 to 5,000 grams/mole.

As representative examples of suitable mobilizers, there may be mentioned hydrocarbon oils, halogenated hydrocarbon oils, phthalic ester oils, vegetable oils, silicone oils, low molecular weight non crystalline polymer greases, such as hydrocarbon polymer greases, low molecular weight polyester greases, polyarylether greases, etc. It is to be understood that the above examples are only illustrative and the use of other mobilizers should be apparent to those skilled in the art from the teachings herein. The preferred mobilizer is a liquid which is not highly viscous, most preferably, a hydrocarbon oil or phthalic ester oil.

A second stabilizer, hereinafter additive B, incorporated into the composition of the invention is a hindered amine which may be provided in the form of the free base, a salt, N-oxide, N-hydroxide or N-nitroxide thereof. In these stabilizers, the nitrogen atom is part of a nonaromatic hetercyclic ring. The nitrogen is flanked by two carbon atoms, each bonded to two lower alkyl groups which may be the same or different, each lower alkyl group containing from 1 to 12 carbon atoms, or to an alicyclic group containing from 4 to 9 carbon atoms, which groups sterically hinder the amine. Preferred hindered amines for use in the compositions of the invention comprise a 5- or 6-membered heterocyclic ring containing the hindered amine nitrogen and optionally another hetero atom preferably nitrogen or oxygen. If the hindered amine is a tertiary amine, the tertiary group may be, for example, an optionally substituted alkyl, aralkyl, or alicyclic group containing from 1 to 12 carbon atoms. One or more of the substituents may be a hindered amine so that the tertiary group may be used to link a plurality of hindered amines. The hindering groups are preferably lower alkyl groups containing from 1 to 4 carbon atoms wherein, most preferably, all four groups are methyl. Preferred hindered amines are 2,2,4,4-tetramethyl piperidine derivatives.

The most preferred hindered amine stabilizer is a hindered bis(4-piperidinyl)diester of a dicarboxylic acid. Representative examples of bis(hindered piperidinyl)diesters acceptable for use in the present invention, but not limited thereby, are the following: bis(2,2,6,6-tetramethyl-4-piperidinyl)-sebacate; bis(1,2,2,6,6-pentamethyl-4-piperidinyl)-2-n-butyl-2-(3,5-di-tert-butyl-4-hydroxybenzyl)malonate; and bis(1,2,2,6,6-pentamethyl-4-piperidinyl)sebacate. These hindered piperidines are commonly referred to as Tinuvin 770, Tinuvin 144, and Tinuvin 292, respectively, and are available from the Ciba Geigy Corporation.

The mobilizing additive may be incorporated into the polymer in a mobilizing amount; generally about 0.1 to 50, preferably about 1 to 20% by weight. For the hindered amine stabilizer, about 0.01 to 5.0, preferably about 0.05 to 3.0% by weight may be used.

In addition to being of narrow molecular weight distribution. The polyolefin of the invention is preferably semicrystalline. Preferred polyolefins have a crystalline content of about 20 to 90, preferably about 40 to 80, most preferably about 45 to 65%. The degree of crystallinity is linearly proportional to the density of the sample and, as known in the art, may be measured with a conventional density gradient column.

The clarifying additive, hereinafter additive C, of the present invention may be a dibenzylidene sorbitol of the following structure:

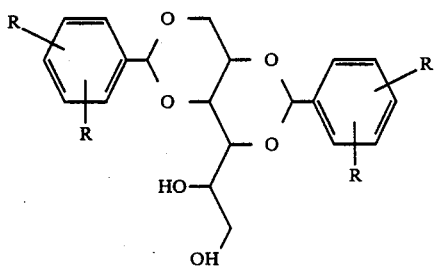

wherein R may be hydrogen, hydroxy, halogen, lower alkoxy, lower alkyl, lower alkylthio, lower alkylsulfoxy or phenylthio wherein the term lower with respect to alkyl or alkoxy is intended to be from 1 to 6 carbon atoms, branched or unbranched. The preferred additives have a lower alkyl thio group in each ring, preferably in the meta or para positions, most preferably in the two para positions.

It is understood with regard to the structural formula set forth above that while only the 1,3:,2,4 isomer is represented, this structure is provided for convenience only and the invention is not limited to isomers of the 1,3:2,4 type, but may include any and all other isomers and mixtures thereof provided that the additive has two benzylidene groups on the sorbitol moiety.

The additives of the invention may be prepared by any suitable sequence of reactions as known in the art. A particularly convenient method is acid catalyzed condensation of the appropriate substituted benzaldehyde with sorbitol. The stoichiometry of this reaction is two moles of aldehyde per mole of sorbitol, and while the preferred ratio of these reactants is at or close to 2:1, other ratios deviating from this preferred value, but still suitable for preparation of the additives, are readily apparent to one ordinarily skilled in the art. Likewise, selection of suitable solvents, acid catalysts, reaction conditions, workup conditions and product isolation procedures are well within the purview of one skilled in the art. A representative non limiting synthetic procedure is given in Example I below. The following list of preferred dibenzylidene sorbitol thioether additives is likewise merely representative:
4,4'-bis(methylthio)dibenzylidene sorbitol
3,3'-bis(methylthio)dibenzylidene sorbitol
4,4'-bis(ethylthio)dibenzylidene sorbitol
3,3'-bis(ethylthio)dibenzylidene sorbitol
4,4'-bis(phenylthio)dibenzylidene sorbitol
3,3'-bis(phenylthio)dibenzylidene sorbitol Condensation of a benzaldehyde and sorbitol under the above conditions leads predominately to the dibenzylidene derivative of the invention. It is appreciated, however, that by product mono- and tribenzylidene derivatives will also be formed, the quantity of the by products formed being variable depending on the reaction workup and purification procedures. In general, it is not necessary to remove these by products because the clarifying and antioxidizing effectiveness of the dibenzylidene sorbitols of the invention are not substantially decreased by the presence of the by-products. It is intended, however, that the additive of the invention consist of 90% or higher of the dibenzylidene sorbitol additive. As known in the art, tribenzylidene by-products may be substantially removed by extraction or trituration of the crude isolate with a nonpolar solvent, and monobenzylidene by products may be removed by recrystallization from a suitable solvent. Such purification techniques are routine and well-known to those skilled in the art.

Clarifying properties are conferred when the additive of the invention is formulated into the polyolefin composition in a guantity within the range of about 0.005 to 2.0% by weight. Higher percentages of additives may be used but generally provide no perceived advantage. The preferred concentration range may be from about 0.05 to 0.5%, most preferably, from about 0.1% to 0.3%.

Other additives as known in the art may be added to provide other desirable properties to the composition. For example, fillers, coloring agents, antistatic materials, wetting agents and the like may be added in suitable quantities providing no deleterious effects in the desired clarity or radiation stability are introduced. In addition, other known clarifying additives, as for example, organic acids and metal salts thereof, such as para-t-butylbenzoic acid, may be incorporated into the composition.

Preparation of the composition of the invention from its constituent parts is routine and may be carried out by any conventional mixing means. Generally, polyolefin pellets and the additive are thoroughly mixed by stirring or tumbling, the mixture melted and the melt pelletized and molded into the shape of the desired article. As representative nonlimiting medical articles which may be fabricated from the composition of the invention, syringes catheters, tube assemblies, tissue culture flasks, and package films may be mentioned. It is, of course, evident that the composition may also be used to make non-medical articles.

Sterilization of the composition or article of the invention is effected by exposure to a sterilizing amount of high energy radiation, for example, electron beam irradiation and particularly gamma irradiation from a cobalt 60-source. A sterilizing amount generally comprises from about 0.5 to 10 megarads, a typical dose being in a range of from about 1.0 to 5.0 megarads and usually from about 1.5 to 3.5 megarads. It is understood that higher doses could be employed but are generally not necessary.

It has been found that, after radiation sterilizing the composition of the invention, the sterilized or irradiated polymer is not embrittled, and moreover, does not develop any substantial embrittlement on aging; i.e., the polymer retains its flexibility. Thus, for example, prior to irradiation, such polymers have a bending angle of at least 90°, and in accordance with the present invention, the irradiated polymer subsequent to irradiation still has a bending angle of about 90°. Even after storage for a long period of time, the resistance to embrittlement of the irradiated polymer of the invention does not substantially diminish.

Clarity of a polyolefin composition is conventionally reported as the haze value. Haze values of the compositions of the invention may be determined in accordance with ASTM procedure D 1003.

In the Table below, polypropylene having an Mw/Mn ratio of 2.8 and a percent crystallinity of 55% is compounded into a composition having the indicated additives. After being sterilized by exposure to 3.0 arads of radiation from a Co-60 source, the compositions gave the indicated haze values.

TABLE I

| No. | Additive | Conc. (wt %) | Haze (%) |
|---|---|---|---|
| 1 | A-Mineral Oil | 4.7 | 12 |
|   | B-Tinuvin 770 | 0.10 | |
|   | C-4,4'-bis(methylthio)-dibenzylidene sorbitol | 0.15 | |
| 2 | A-Mineral Oil | 4.7 | 58 |
|   | B-Tinuvin 770 | 0.10 | |
| 3 | A-Tinuvin 770 | 0.10 | 12 |
|   | B-4,4'-bis(methythio)-dibenzylidene sorbitol | 0.15 | |

The invention will be further described with respect to the following examples; however, the scope of the claims is not to be limited thereby.

EXAMPLE I

Determination of Haze Value

Pelletized polypropylene (500 g) of narrow molecular weight range was shaken with 4,4'-bis-(methylthio)-dibenzylidene sorbitol (2.5 g, finely powered) to coat the pellets electrostatically. The pellets were then extruded through a single screw extruder at 210° C., cooled in a water bath, and re-pelletized. The new pellets were then molded into step plagues 50×75 mm in overall dimension by injection molding. The upper step was 0.080 inches thick while the lower step was 0.040 inches thick. The haze values reported in Table I were from 0.040 inch step and were measured using ASTM Method D1003.

EXAMPLE II

Syringe Barrel Flange Bending for Determination of Embrittlement

Molded 3 cc polypropylene syringe barrels were irradiated at 0.5 megarad/hour to a total dose of 0,2,3,5 and 7 megarad. Immediately after irradiation, and after storage away from direct sunlight for 3,6,9 and 12 months, the barrel flanges were tested for embrittlement. A minimum of two barrels (4 flanges) were tested for each radiation dose and for each time interval. The testing equipment was an Instron Tensile Tester, Model 1122, load cell 0–50 kg capacity equipped with standard Instron accessories, a microprocessor and a flange bending device.

The barrel flange was secured in the Instron holder with the barrel 1 mm from the anvil face. The Instron was calibrated to traverse 90° at a test speed of 83 cm/min at a chart speed of 100 cm/min. The flange was bent through 90° followed by rotation and bending of the other flange through 90° while observing for breakage of the flange due to embrittlement.

EXAMPLE III

Figure 2:
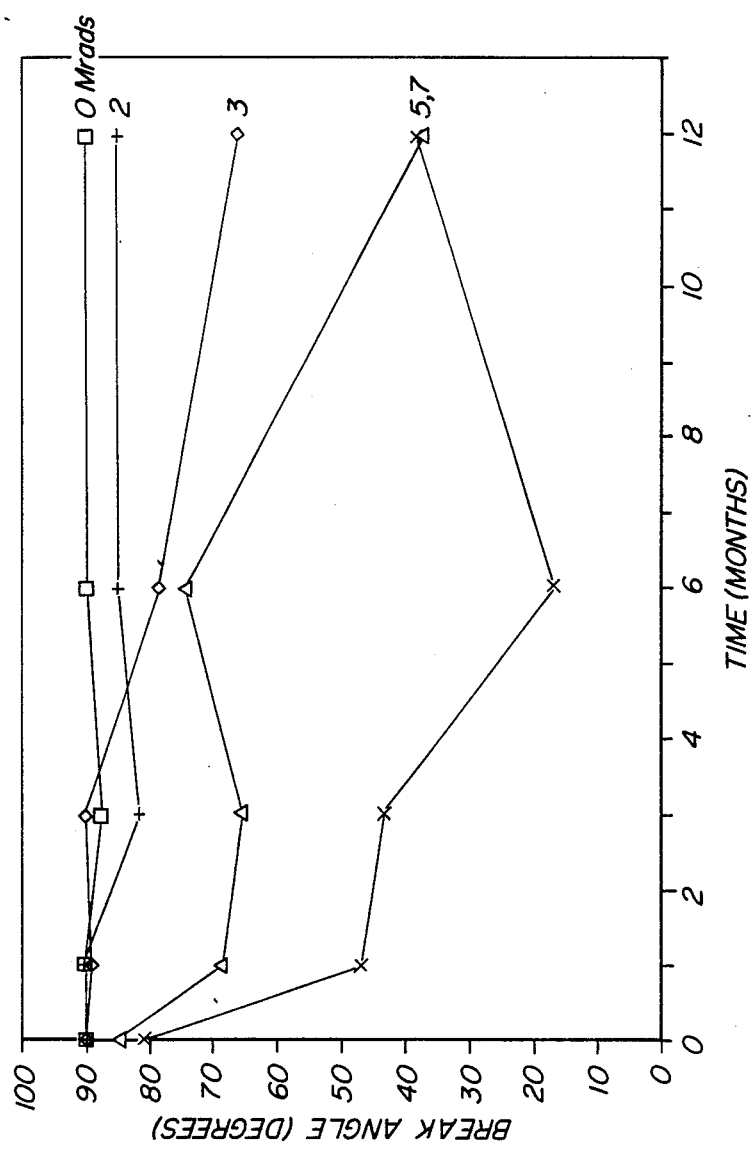
FIG. 2 shows resistance to embrittlement of the polypropylene of FIG. 1 without the mobilizing additive.

A sample of narrow molecular weight distribution polypropylene having a ratio of weight average molecular weight to number average molecular weight (Mw/Mn) of 2.8 containing 4.7% of a mobilizing additive (hydrocarbon oil) was irradiated to 2,3,5 and 7 megarads. Immediately following irradiation, and after 12 months aging, the sample was still flexible, as shown in FIG. 1. For comparison, the same polypropylene sample containing no mobilizing additive was shown to break at 3,5 and 7 megarads after 12 months aging as shown in FIG. 2.

Figure 3:
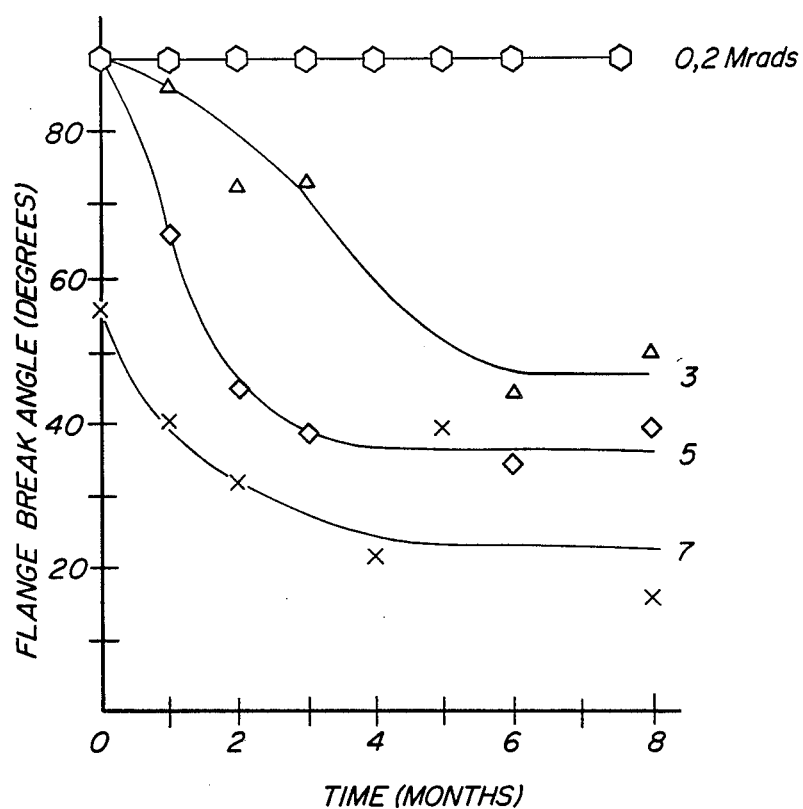
FIG. 3 shows resistance to embrittlement of a broad molecular weight range polypropylene containing the mobilizing additive of FIG. 1.

A broad molecular weight distribution polypropylene, Mw/Mn=10, containing 4.7% of the same mobilizing additive could not withstand more than 2 megarads before embrittlement, as shown in FIG. 3.

A sample of narrow molecular weight distribution polypropylene, having a ratio of weight average molecular weight to number average molecular weight (Mw/Mn) of 2.8, containing 0.25% of 4,4'-bis(methythio)dibenzylidene sorbitol and 4.7% of hydrocarbon oil gave a high clarity resin having the flange break data shown in FIG. 4 after irradiation with 0 to 7 megarads and 12 months aging.

It is seen by comparison of FIGS. 1 and 4 that the improved clarity gained by inclusion of the clarifying agent is a tradeoff against a somewhat reduced resistance to embrittlement. On the other hand, comparison of FIGS. 2 and 4 shows that the resistance to embrittlement of the composition of the invention is still substantially better than that of the polypropylene of FIG. 2, which is the resin used in commercial syringes sold by Becton, Dickinson and Company under the tradename Plastipak ®.

What is claimed is:

1. A composition comprising a polyolefin having a crystalline content of about 20 to 90 percent and a weight distribution wherein the ratio of the weight average molecular weight to the number average molecular weight is no greater than 6, a mobilizing amount of a liquid mobilizer compatible with said polyolefin having a density of about 0.6 to 1.9 grams per cubic centimeter, a radiation stabilizing amount of a hindered piperidine stabilizer and a clarifying amount of a dibenzylidene sorbitol alkyl thioether clarifier.

2. The composition of claim 1 further comprising about 0.1 to 10% of an additional polymer.

3. The composition of claim 1 wherein said polyolefin is selected from the group consisting of polyethylene, polypropylene, polymethylpentene, polytetrafluoroethylene and copolymers thereof.

4. The composition of claim 1 wherein said mobilizing additive is selected from the group consisting of a hydrocarbon oil phthalic ester, polymer grease, vegetable oil and silicone oil.

5. The composition of claim 1 wherein said stabilizer is a bis(4-piperidinyl) diester of a dicarboxylic acid.

6. A composition comprising a semicrystalline polyolefin having a weight distribution wherein the ratio of the weight average molecular weight to the number average molecular weight is no greater than 9.0, a mobilizing amount of a noncrystalline mobilizing additive which is compatible with said polyolefin, and which increases the free voluem of said polyolefin, a radiation stabilizing amount of a hindered amine stabilizer and a clarifying amount of thioether dibenzylidene sorbitol clarifer.

7. A composition comprising polypropylene having a crystalline content of 30 to 70 percent and a weight distribution wherein the ratio of the weight average molecular weight to the number average molecular weight is about 2 to 4, a mobilizing amount of a substantially nonviscous liquid mobilizer selected from the group consisting of a hydrocarbon oil and a phthalic ester oil, a radiation stabilizing amount of a hindered bis(4-piperidinyl) diester of a dicarboxylic acid stabilizer, and a clarifying amount of 4,4'-bis(methylthio)-dibenzylidene sorbitol.

* * * * *